(12) United States Patent
Patwardhan et al.

(10) Patent No.: US 10,617,305 B2
(45) Date of Patent: Apr. 14, 2020

(54) DERMATOSCOPE DEVICES

(71) Applicant: Canfield Scientific, Incorporated, Fairfield, NJ (US)

(72) Inventors: Sachin V. Patwardhan, Morris Plains, NJ (US); Daniel Eric DiGregorio, Paterson, NJ (US); Athula Mandanayake, Kinnelon, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 1233 days.

(21) Appl. No.: 14/193,824

(22) Filed: Feb. 28, 2014

(65) Prior Publication Data
US 2014/0243685 A1    Aug. 28, 2014

Related U.S. Application Data

(60) Provisional application No. 61/770,954, filed on Feb. 28, 2013.

(51) Int. Cl.
*A61B 5/00* (2006.01)
*G02B 21/36* (2006.01)

(52) U.S. Cl.
CPC ............. *A61B 5/0077* (2013.01); *A61B 5/44* (2013.01); *G02B 21/368* (2013.01); *A61B 5/6898* (2013.01); *G02B 21/361* (2013.01)

(58) Field of Classification Search
CPC ......... A61B 5/0077; A61B 5/441; A61B 5/44; A61B 2560/0443; A61B 5/0059
See application file for complete search history.

(56) References Cited

U.S. PATENT DOCUMENTS 4,988,158 A * 1/1991 Yamamoto ............ G02B 21/12
 385/33
6,032,071 A   2/2000 Binder
(Continued)

FOREIGN PATENT DOCUMENTS

WO    WO 9318433 A1 *  9/1993 ............. G03B 17/48

OTHER PUBLICATIONS

MedGadget, written by Darren Quick, "Handyscope turns an iPhone into a digital dermoscope". Web Address: https://newatlas.com/handyscope-turns-an-iphone-into-a-digital-dermoscope/17660/ . 4 pages. Dated Jan. 23, 2011. (Year: 2011).*
(Continued)

*Primary Examiner* — James M Kish

(57) ABSTRACT

A dermatoscope has a generally circular viewing opening, a plurality of light sources including first and second groups of light sources arranged about the viewing opening, a first polarizer for polarizing light passing through the viewing opening, and a second polarizer for polarizing light emitted from the first group of light sources, wherein the first and second groups of light sources are arranged at different distances from a center of the viewing opening so that light from the second group of light sources is not polarized by the second polarizer. A further dermatoscope has a head portion including a generally circular viewing opening, and at least one light source arranged proximate to the viewing opening; and a body portion including an image capture device, wherein the head portion is pivotally attached to the body portion selectively allowing alignment of the center of the viewing opening with the center of the field of view of the image capture device. Yet a further dermatoscope has a generally circular viewing opening, a selectively extendable element that can be selectively extended coaxially with the viewing opening, and a contact element for contacting a surface to be viewed, the contact element being removably (Continued)

attachable to a distal end of the selectively extendable element.

18 Claims, 19 Drawing Sheets

(56) References Cited

U.S. PATENT DOCUMENTS

| | | | | |
|---|---|---|---|---|
| 6,118,476 | A | 9/2000 | Morito et al. | |
| 6,587,711 | B1* | 7/2003 | Alfano | A61B 5/0068 600/410 |
| 7,167,244 | B2* | 1/2007 | Mullani | A61B 5/0059 356/369 |
| 7,369,692 | B2* | 5/2008 | Shirai | A61B 5/0059 348/77 |
| 7,986,987 | B2* | 7/2011 | Bazin | A61B 5/448 600/407 |
| 8,588,605 | B2* | 11/2013 | Harris | G02B 27/28 396/544 |
| 2003/0045799 | A1* | 3/2003 | Bazin | A61B 5/448 600/476 |
| 2004/0062056 | A1 | 4/2004 | Heine et al. | |
| 2004/0174525 | A1 | 9/2004 | Mullani | |
| 2004/0201846 | A1* | 10/2004 | Mullani | A61B 5/0059 356/369 |
| 2006/0139640 | A1* | 6/2006 | Mullani | A61B 5/445 356/369 |
| 2007/0248343 | A1* | 10/2007 | Yamamoto | G02B 7/023 396/76 |
| 2008/0147053 | A1 | 6/2008 | Kang et al. | |
| 2010/0225429 | A1* | 9/2010 | Tsai | H01F 7/0247 335/219 |
| 2011/0043683 | A1* | 2/2011 | Beach | G02B 13/0065 348/373 |
| 2011/0304705 | A1 | 12/2011 | Kantor et al. | |
| 2012/0236425 | A1* | 9/2012 | O'Neill | G02B 7/14 359/827 |
| 2013/0028591 | A1* | 1/2013 | Hicks | G03B 41/00 396/544 |
| 2013/0177304 | A1* | 7/2013 | Chapman | G03B 17/565 396/533 |
| 2014/0078594 | A1* | 3/2014 | Springer | G02B 7/16 359/672 |

OTHER PUBLICATIONS

EPO as ISA, Invitation to Pay Additional Fees, International App. No. PCT/US2014/019510, dated Jun. 13, 2014.
EPO as ISA, International Search Report and Written Opinion of the ISA, International App. No. PCT/US2014/019510, dated Aug. 1, 2014.

* cited by examiner

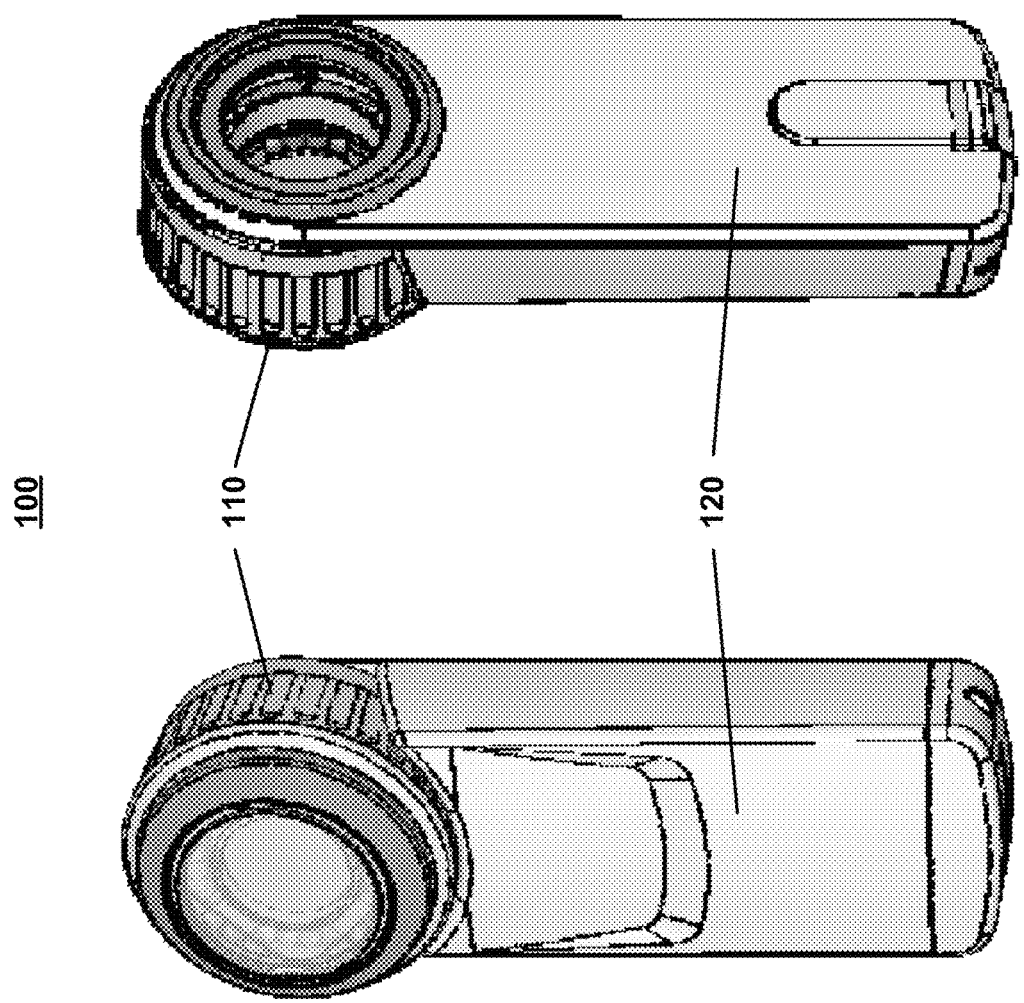

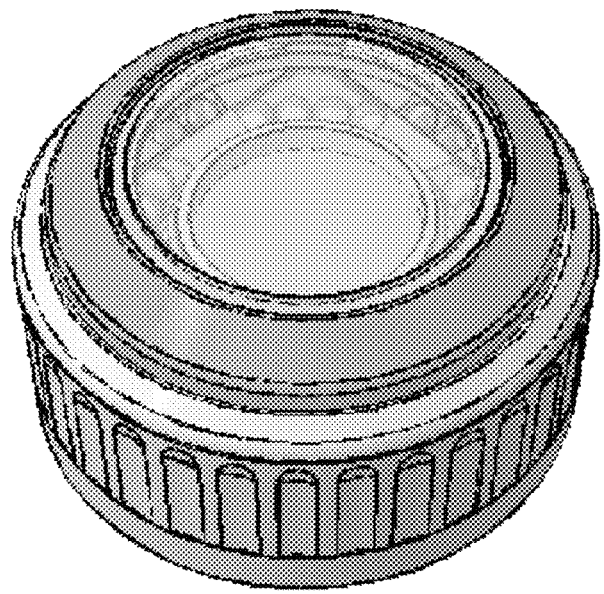
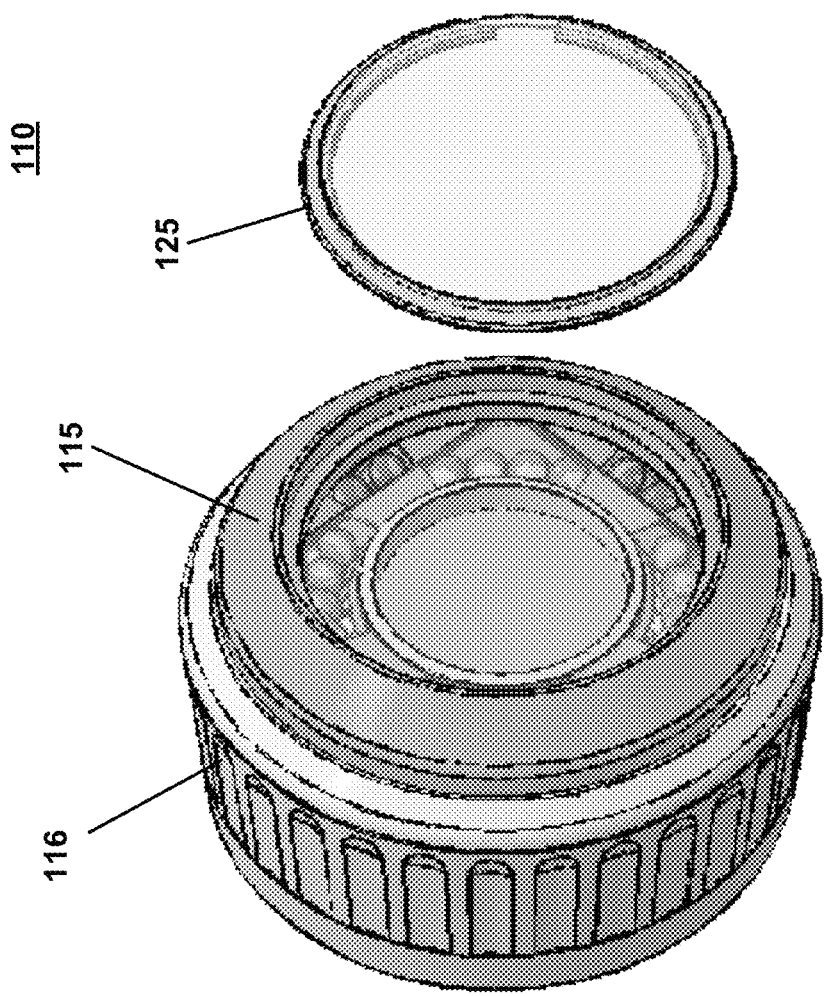
*FIG. 4B*
*FIG. 4A*

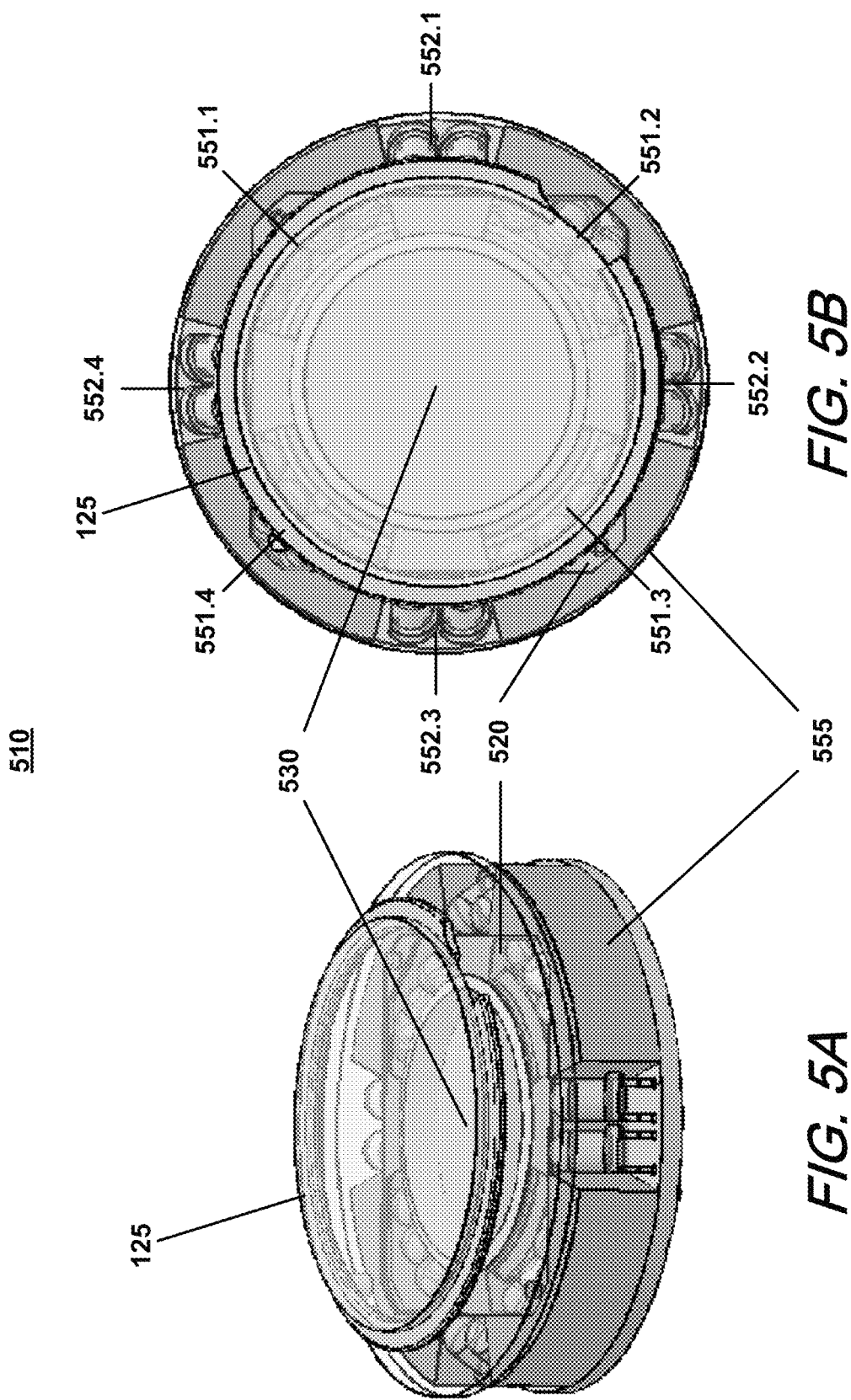

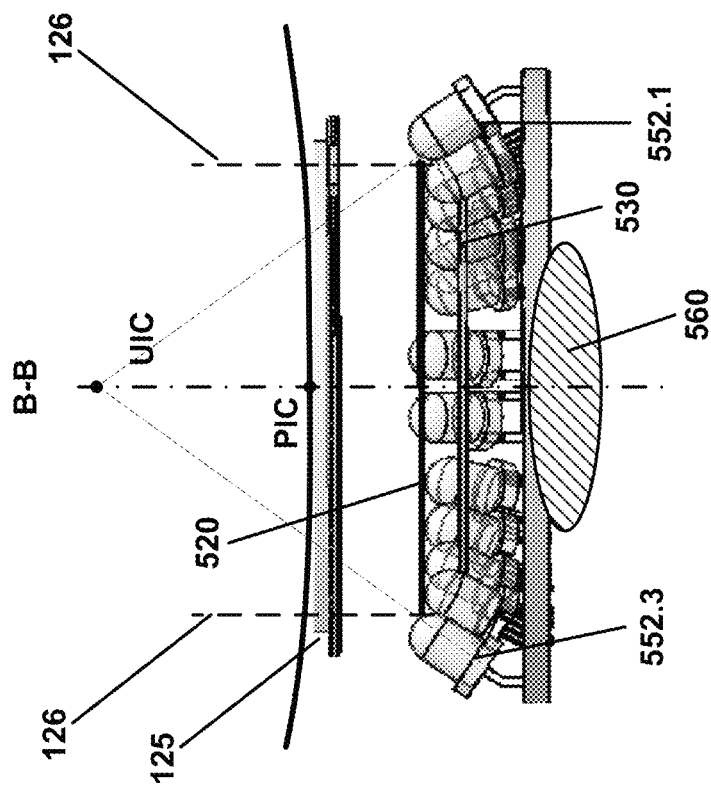
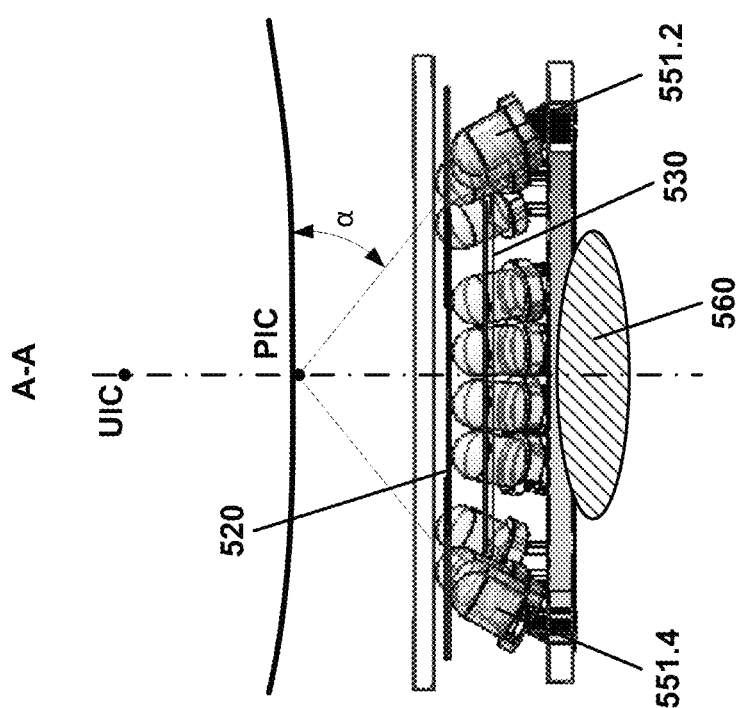
FIG. 5F
FIG. 5E

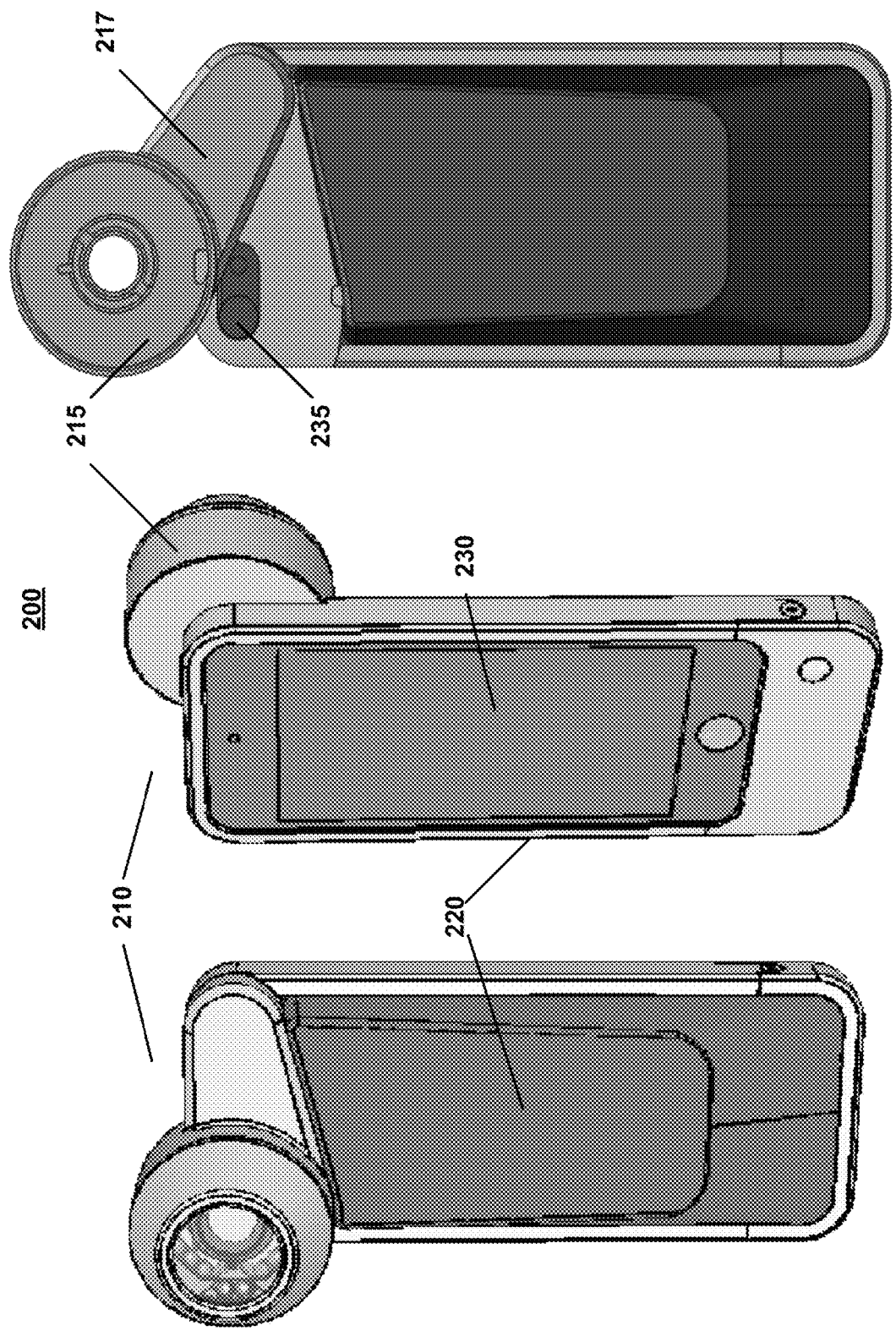
*FIG. 6A*  *FIG. 6B*  *FIG. 6C*

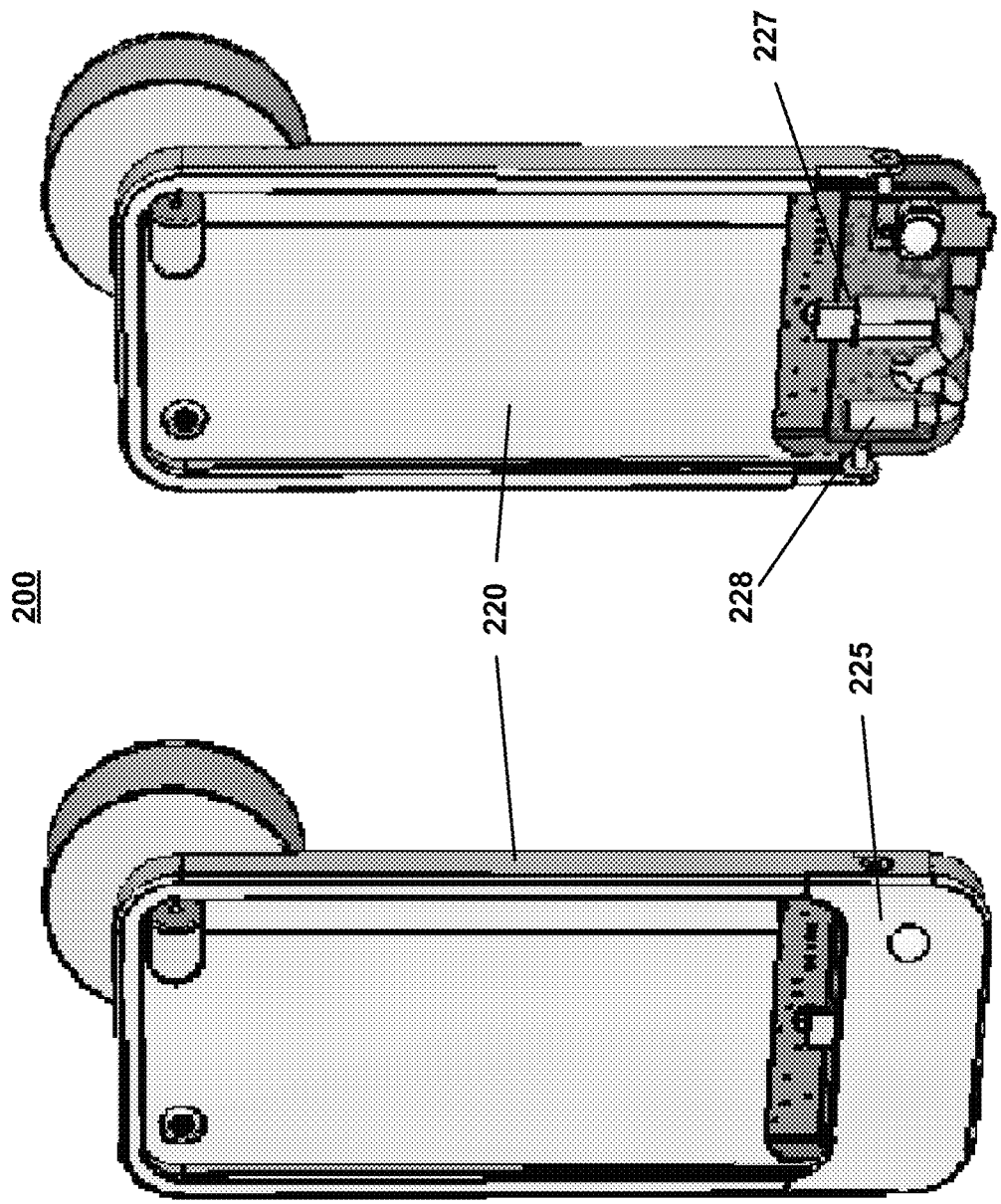

DERMATOSCOPE DEVICES

RELATED PATENT APPLICATIONS

The present application claims priority from U.S. Provisional Patent Application No. 61/770,954 filed on Feb. 28, 2013, which is incorporated herein by reference in its entirety.

FIELD OF THE INVENTION

The present invention relates generally to devices for viewing and imaging tissue, particularly skin.

BACKGROUND INFORMATION

Devices for examining skin are commonly referred to as dermatoscopes. A typical dermatoscope is handheld and may include a magnifier, a light source and a transparent contact plate. A liquid medium applied between the transparent contact plate and the skin allows inspection of the skin unobstructed by reflections from the surface of the skin. Some dermatoscopes use polarized light to minimize skin surface reflections. Some dermatoscopes can be attached to a camera, thereby allowing the capture of images through the dermatoscope.

SUMMARY OF THE INVENTION

A dermatoscope is disclosed having a generally circular viewing opening, a plurality of light sources including first and second groups of light sources arranged about the viewing opening, a first polarizer for polarizing light passing through the viewing opening, and a second polarizer for polarizing light emitted from the first group of light sources, wherein the first and second groups of light sources are arranged at different distances from a center of the viewing opening so that light from the second group of light sources is not polarized by the second polarizer.

A further dermatoscope is disclosed having a head portion including a generally circular viewing opening, and at least one light source arranged proximate to the viewing opening; and a body portion including an image capture device, wherein the head portion is pivotally attached to the body portion selectively allowing alignment of the center of the viewing opening with the center of the field of view of the image capture device.

Yet a further dermatoscope is disclosed having a generally circular viewing opening, a selectively extendable element that can be selectively extended coaxially with the viewing opening, and a contact element for contacting a surface to be viewed, the contact element being removably attachable to a distal end of the selectively extendable element.

The aforementioned dermatoscopes as well as others are disclosed herein.

BRIEF DESCRIPTION OF THE DRAWINGS

The following description of various embodiments of the present disclosure can best be understood when read in conjunction with the following drawings:

FIGS. 1A and 1B show front and back perspective views, respectively, of an exemplary dermatoscope device.

FIGS. 4A through 4D show an exemplary arrangement in which a contact viewing element is removably attached to a head portion of the device of FIGS. 1A-F.

FIGS. 5A through 5F show an exemplary illumination and polarization sub-assembly of the device of FIGS. 1A-F.

FIGS. 6A through 6I show various views of a further exemplary dermatoscope device, the device having a mobile computing device integrated therewith.

FIGS. 7A and 7B show rear perspective views of the device of FIGS. 6A-I with the mobile computing device removed.

DETAILED DESCRIPTION

FIGS. 1A and 1B show front and back perspective views, respectively, of an exemplary device 100 for viewing and imaging tissue such as human skin. The dermatoscope device 100 generally comprises a head portion (or "head") 110 and a body portion (or "body") 120. The head 110 serves to provide illumination, viewing, and/or imaging functionality. The body 120 is configured and sized to be held by hand as a user views the target tissue via the head 110. The body 120 also houses circuitry and a power source, such as one or more batteries, for controlling and driving the illumination provided by the head 110. In exemplary embodiments, illumination is provided by one or more groups of one or more light emitting diodes (LEDs) each. The LEDs are preferably arranged about a central viewing opening in the head 110 through which the target tissue is viewed. One or more optical elements such as a lens or lenses may be arranged along the central opening to provide a desired magnification or field of view.

Figure 1F:
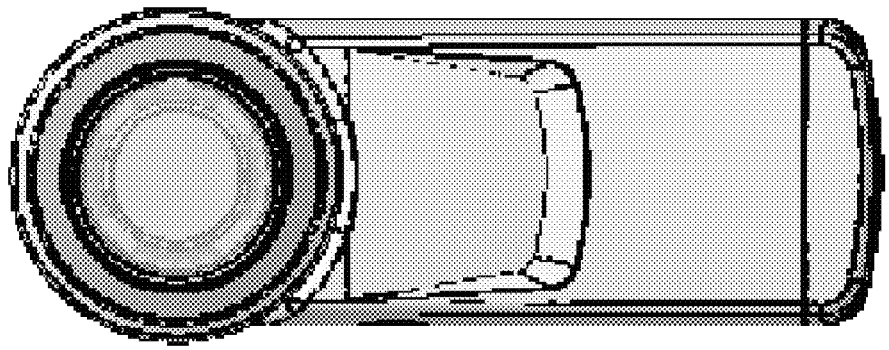
FIGS. 1E and 1F show side elevation and front plan views, respectively, of the device.
Figure 1D:
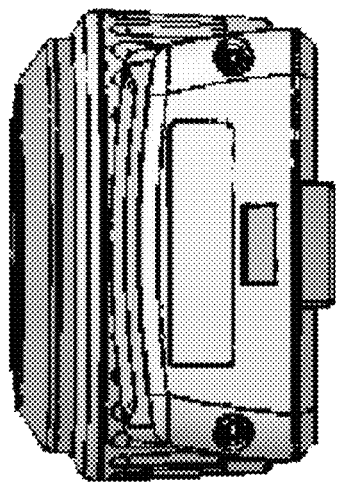
FIGS. 1C and 1D show top and bottom elevation views, respectively.
Figure 1E:
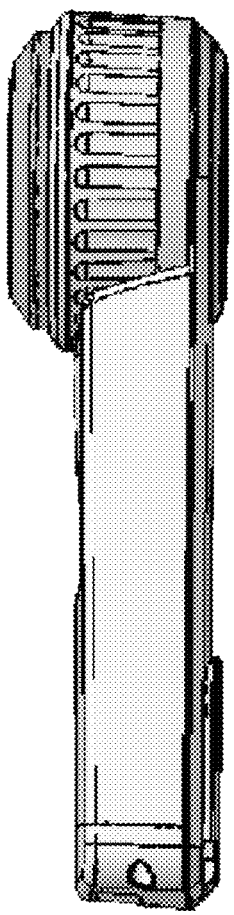
Figure 1C:
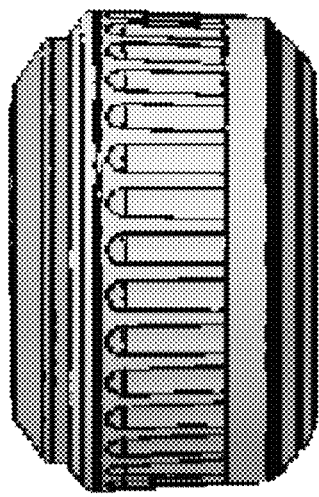

FIGS. 1C and 1D show top and bottom elevation views, respectively, of the device 100. FIG. 1E shows a side elevation view and FIG. 1F shows a front plan view of the device 100.

Figure 2C:
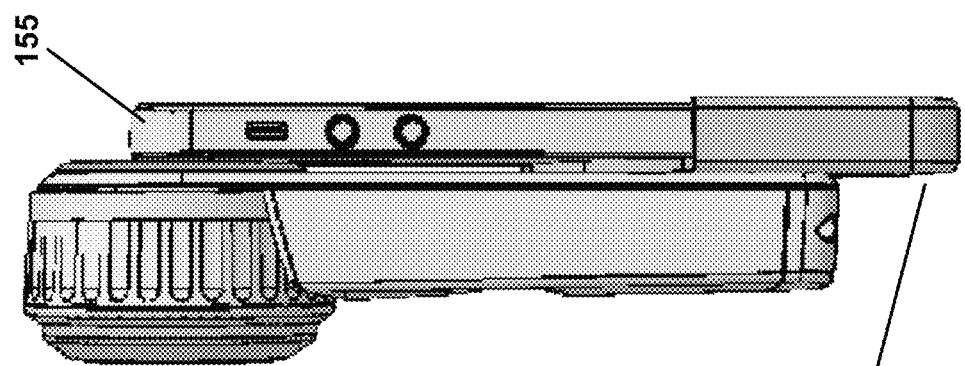
FIGS. 2A through 2G show the exemplary device of FIGS. 1A-F detailing an exemplary arrangement for coupling an image capture device thereto.
Figure 2B:
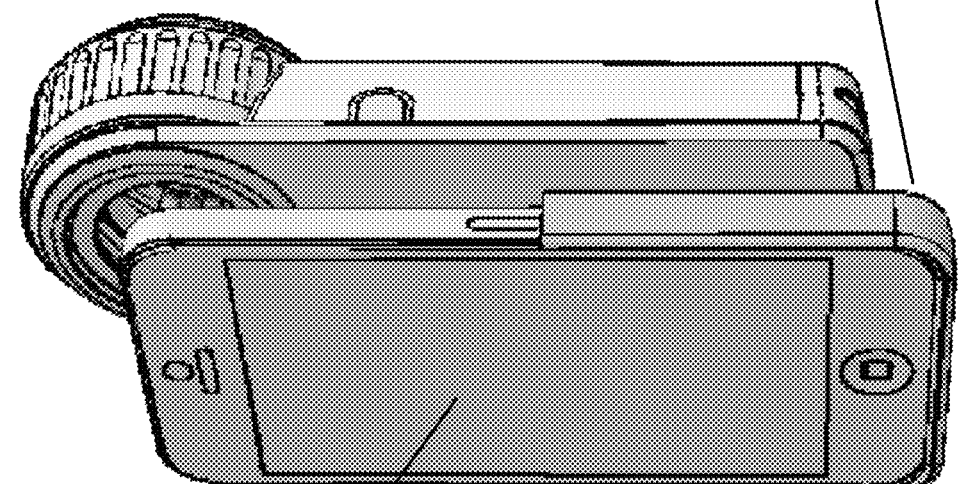
Figure 2A:
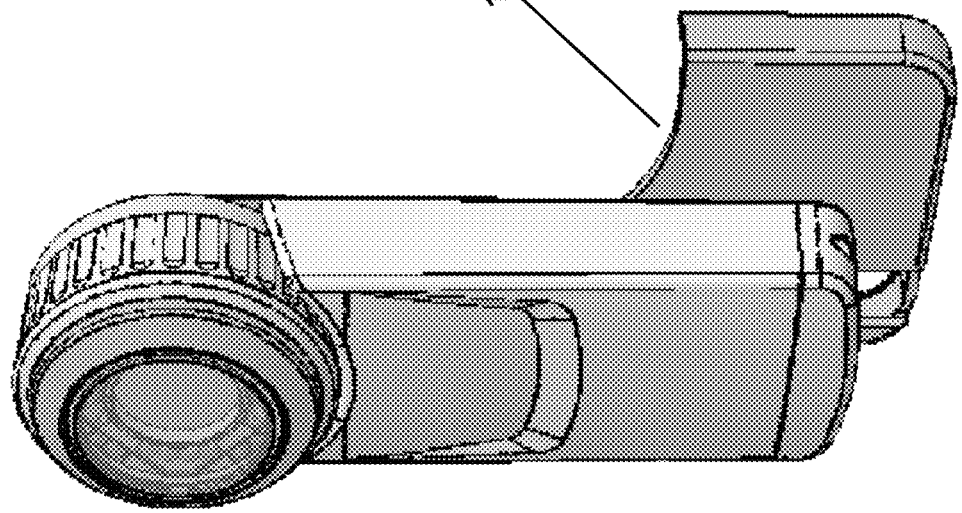
Figure 2E:
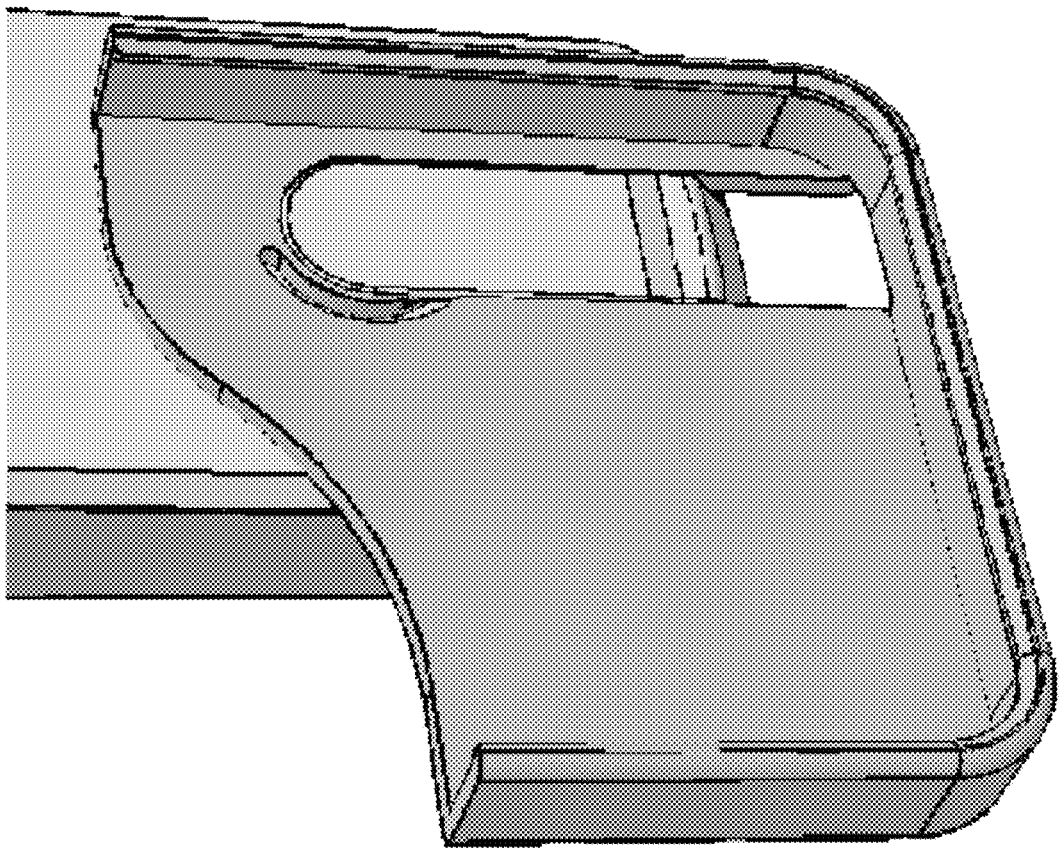
Figure 2D:
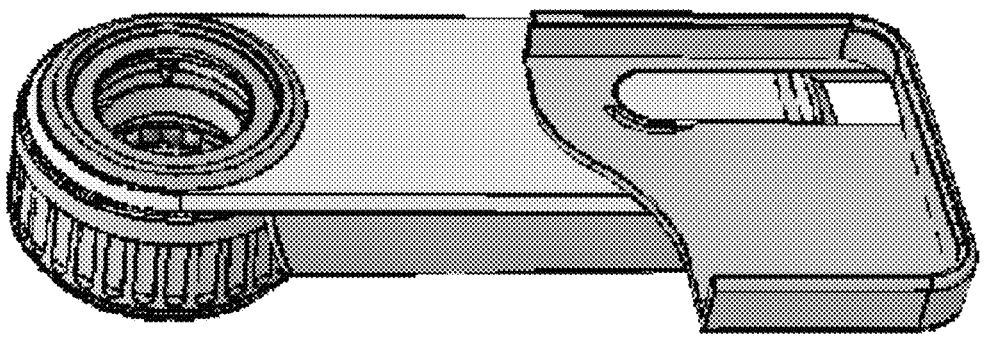
Figure 2G:
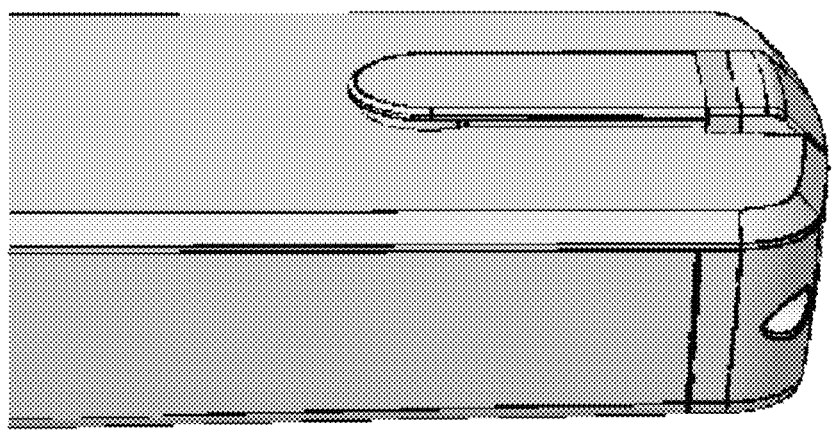
Figure 2F:
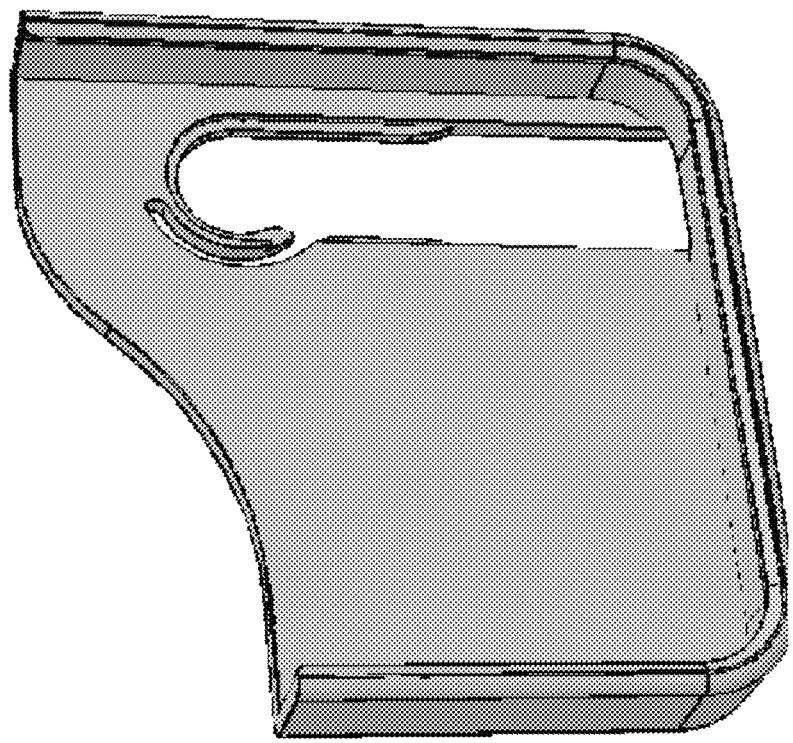

FIGS. 2A through 2E show the device 100 with an attachment 150 attached thereto for mounting a device 155 behind the device 100. It is contemplated that device 155 is a smartphone, mobile computing device, or the like, with image capture capabilities. FIG. 2A shows a front perspective view of the device 100 with the attachment 150 but with no device 155. FIG. 2B shows a rear perspective view of the device 100 with the attachment 150 holding a device 155 behind the device 100, and FIG. 2C shows a side view of the arrangement of FIG. 2B. FIG. 2D shows a rear perspective view of the device 100 with the attachment 150 attached thereto and FIG. 2E shows an enlargement of the bottom portion of FIG. 2D showing the mating of the device 100 and attachment 150 in isolation. FIGS. 2F and 2G show enlarged rear perspective views of the attachment 150 and device 100 respectively.

As shown in the aforementioned figures, the attachment 150 is generally in the shape of a partial sleeve for receiving therein device 155. When mated to device 100 and with the device 155 seated within attachment 150, devices 100 and 155 are held in such a spatial relationship so as to allow the image capturing optics of the device 155 to capture images via the head 110 of the device 100. In the exemplary embodiment shown, it is contemplated that the device 155 has a camera opening in the upper left hand corner of the backside thereof, i.e., the side facing the device 100. When devices 100 and 155 are mated, the center of the field of view of the camera of device 155 is preferably in alignment with the optical center of the head 110.

Figure 3B:
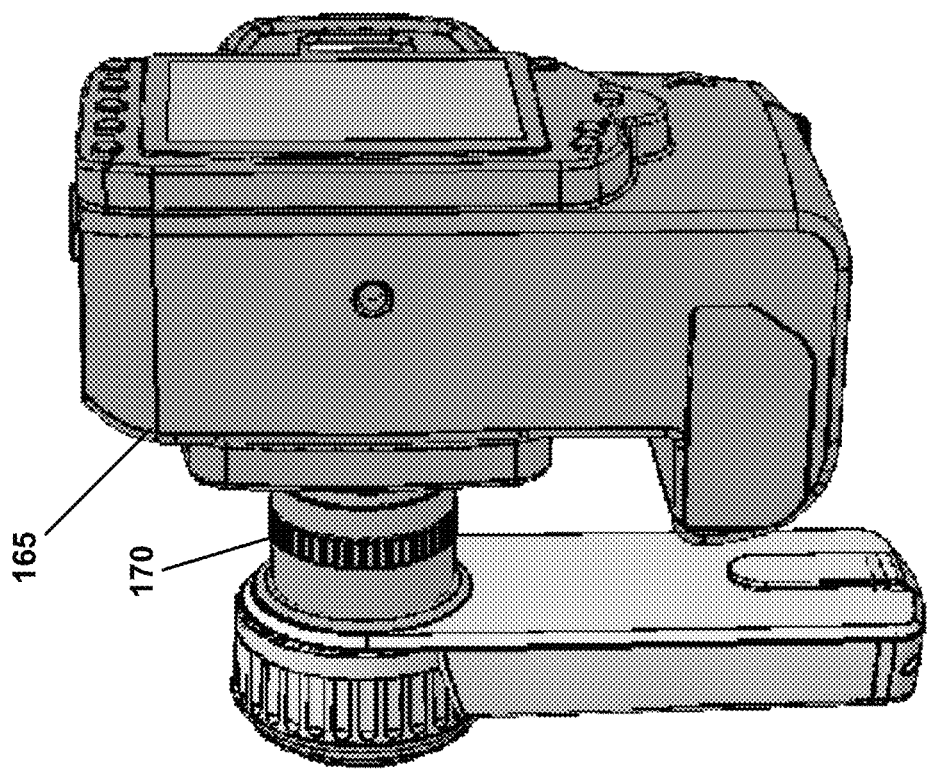
FIGS. 3A through 3E show the exemplary device of FIGS. 1A-F detailing a further exemplary arrangement for coupling an image capture device thereto.
Figure 3A:
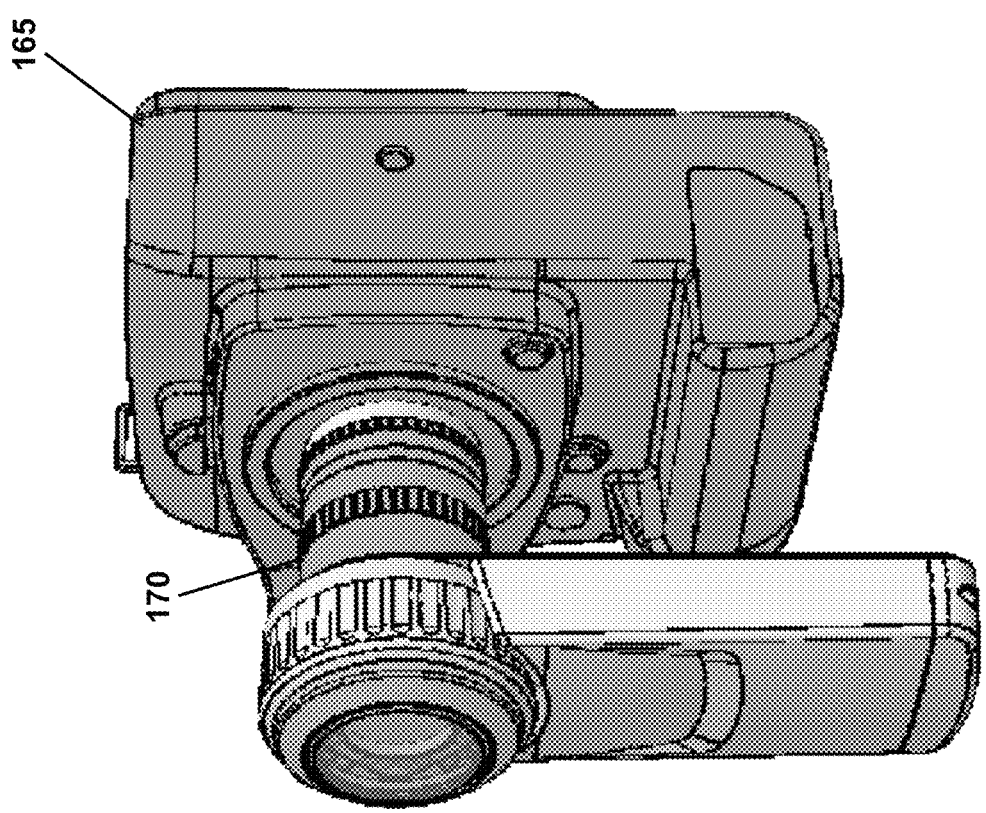

FIGS. 3A and 3B show front and rear perspective views of a further arrangement for attaching a camera 165 to device 100. In the arrangement shown, a coupler 170 is used to mechanically and optically couple the camera 165 with the head 110 of the device 100. In an exemplary embodiment, the coupler 170 and the head 110 attach together with a complementary threaded engagement. The coupler 170 attaches to the camera 165 by the attachment arrangement (e.g., bayonet, C-mount) provided on the camera 165.

Figure 3E:
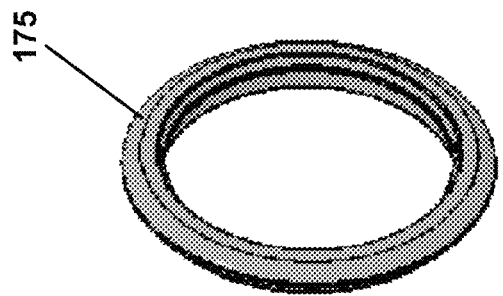
Figure 3D:
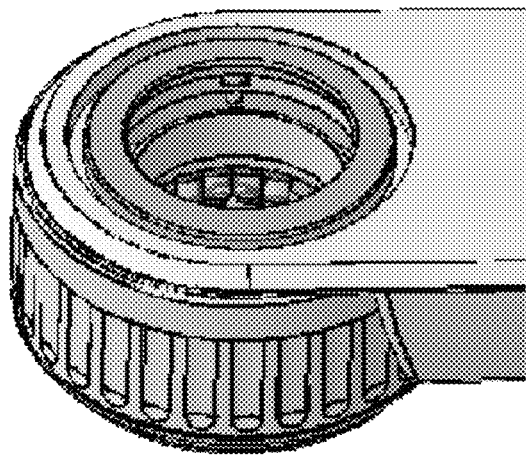
Figure 3C:
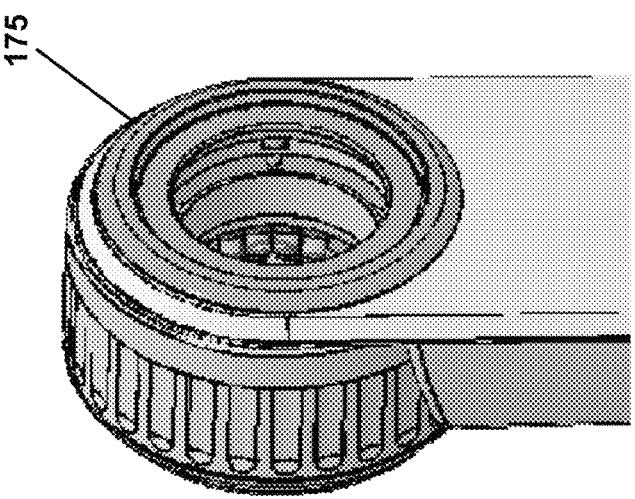

FIGS. 3C and 3D show, in greater detail, the back of the head 110 of the device 100. FIG. 3E shows a removable ring 175 that engages a mating threaded portion on the back of the head 110. When the ring 175 is removed, the coupler 170 can be threaded onto the back of the head 110.

FIGS. 4A and 4B show an exemplary arrangement in which a contact viewing element 125 is removably attached to the head 110 of the device 100. More specifically, the contact viewing element 125 magnetically attaches to an element 115 of the head 110. FIG. 4A shows the contact viewing element 125 removed, whereas FIG. 4B shows the contact viewing element 125 seated within a complementary recess of element 115. With contact viewing element 125 attached, contact viewing/imaging can be performed (typically with a tissue interfacing, i.e., refractive index matching, fluid such as alcohol, oil, gel, or the like). Non-contact viewing/imaging is typically done with the contact viewing element 125 removed.

The head 110 is configured so that the element 115 can be selectively extended or retracted axially from the head by rotation of an outer ring 116. In either contact or non-contact imaging mode, it is contemplated that the element 115 will rest against the surface of the target skin. Element 115 can be selectively extended or refracted so that the skin and/or skin features of interest are in focus. The amount of extension depends on the viewer's eyesight/vision. In an exemplary embodiment, the extension/retraction of element 115 has a travel range to allow vision corrective adjustment from −3.0 to +3.0 diopter.

In operation, the viewer would adjust the extension of element 115 per their eyesight with the element 115 touching the skin. As such, once adjusted for focus, it is contemplated that the element 115 will touch the skin when conducting either contact or non-contact viewing. This allows for quick transition from one location to another, and relieves the user of trying to hold the device in air at a specific distance from the skin in order to maintain focus. The user can thus rest the device against the skin while reproducibly achieving proper focus, even when changing skin locations and viewing modes. When conducting non-contact viewing, the user also has the option of viewing the skin without having the element 115 touch the skin. The contact viewing element 125 seats into the element 115 so that once the height of element 115 is adjusted, both contact and non-contact modes will be in focus. Of course for non-contact viewing, the user has the option of retracting element 115 and not relying on it to provide the appropriate distance for achieving focus.

Figure 4D:
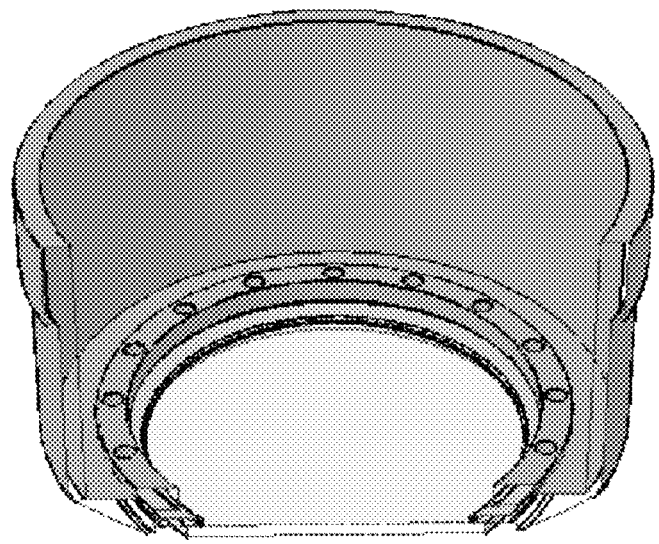
Figure 4C:
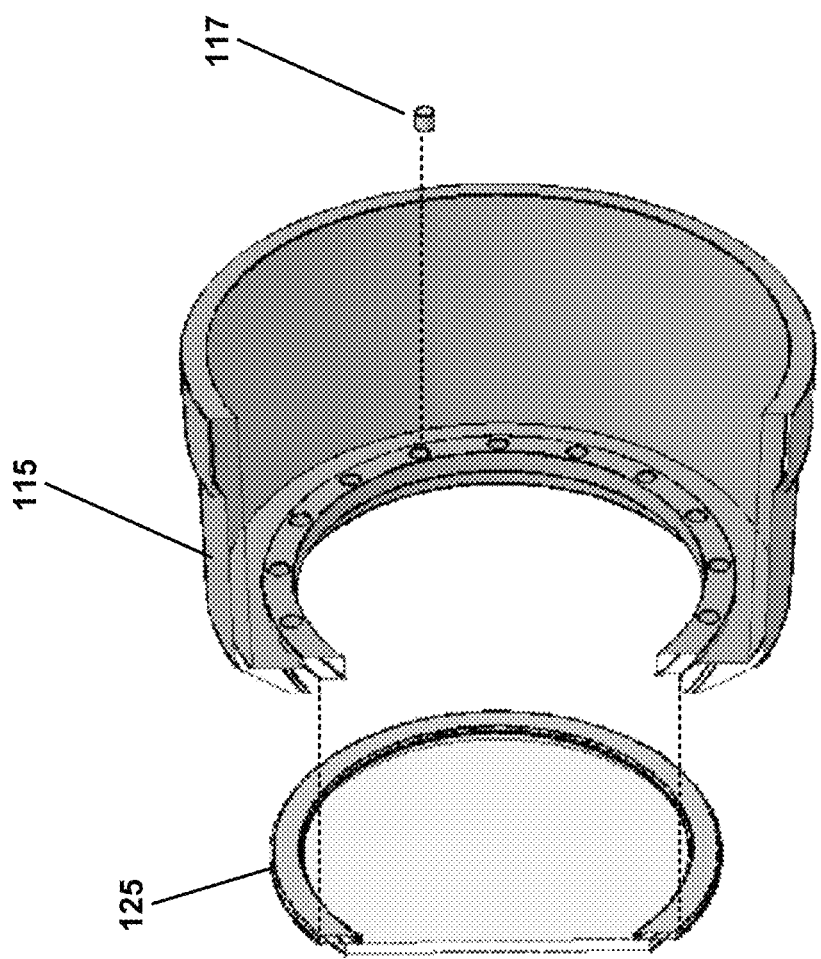

FIGS. 4C and 4D are rear perspective cross-sectional views of element 115, in isolation, and contact viewing element 125, apart, and attached, respectively. As shown in FIG. 4C, element 115 is provided with a plurality of recesses or pockets for receiving therein a corresponding plurality of magnets 117. Only one magnet is shown for clarity. Contact viewing element 125 comprises a transparent plate, such as glass, attached to a metallic ring along all or a portion of the perimeter of the transparent plate. While a magnetic arrangement is shown for removably attaching contact viewing element 125 to element 115, other attachment arrangements employing, for example, friction, threaded or spring action engagement, among others, are possible.

FIGS. 5A and 5B show isometric and plan views respectively of an illumination and polarization sub-assembly 510 which is located in the head 110 of the device 100. Sub-assembly 510 includes a plurality of illumination sources, such as light emitting diodes (LEDs) arranged about a central opening through which the target tissue is viewed. In the exemplary embodiment shown, there are 24 LEDs arranged in four groups 551 of four LEDs each and in four groups 552 of two LEDs each. The 16 LEDs in the four groups 551.1-551.4 are arranged generally at a first distance from the center of the central opening, whereas the eight LEDs in the four groups 552.1-552.4 are arranged generally at a second distance from the center of the central opening, with the second distance being greater than the first distance. A variety of illumination configurations, including the type of illumination elements and the grouping thereof (e.g., the number of groups, the number of illumination elements in each group, spacing) are contemplated by the present disclosure.

Sub-assembly 510 includes an illumination polarizer 520 configured so that light emitted from the LED groups 551.1-551.4 passes through the illumination polarizer 520 whereas light emitted from the LED groups 552.1-552.4 does not pass through the illumination polarizer 520. In the exemplary embodiment shown, illumination polarizer 520 has a generally polygonal shape, e.g., square or octagon, with a central opening corresponding to the central opening of the sub-assembly 510. With reference to FIGS. 5A through 5D, note that the placement of the LED groups and the shape of the polarizer 520 allow light emitted from the LED groups 551 to pass through the polarizer 520 and light emitted from the LED groups 552 to clear the polarizer 520 without being polarized. Additionally, the angles at which the LEDs are pointed relative to the plane of the circuit board on which they are mounted, can also be used to advantage in this regard, with the LEDs of the groups 551 being arranged at a more acute angle than the LEDs of the groups 552. It should also be noted that other than a central opening and possibly one or more additional openings that may be provided for seating and/or alignment purposes, polarizer 520 can be implemented with no additional openings.

In exemplary embodiments, the LEDs can be energized in any suitable combination, including individually or in various groupings. In exemplary embodiments, the LED groups 551 and the LED groups 552 can be energized independently of each other.

Sub-assembly 510 includes a shroud component 555 having vertical walls between adjacent groups of LEDs. The vertical walls serve to eliminate or minimize the leakage of light from adjacent groups of LEDs.

Sub-assembly 510 also includes a viewing polarizer 530 arranged generally coaxially with the central opening of the sub-assembly so that light passing through the central opening is polarized. An optical element, such as lens 560 is also arranged generally coaxially with the central opening of sub-assembly 510, as shown in FIGS. 5E and 5F. In an exemplary embodiment, lens 560 provides 10× magnification.

In exemplary embodiments, illumination polarizer 520 and viewing polarizer 530 are arranged so that their polarization orientations are different. In exemplary embodiments, said orientations are orthogonal.

Figures 5C, 5D:
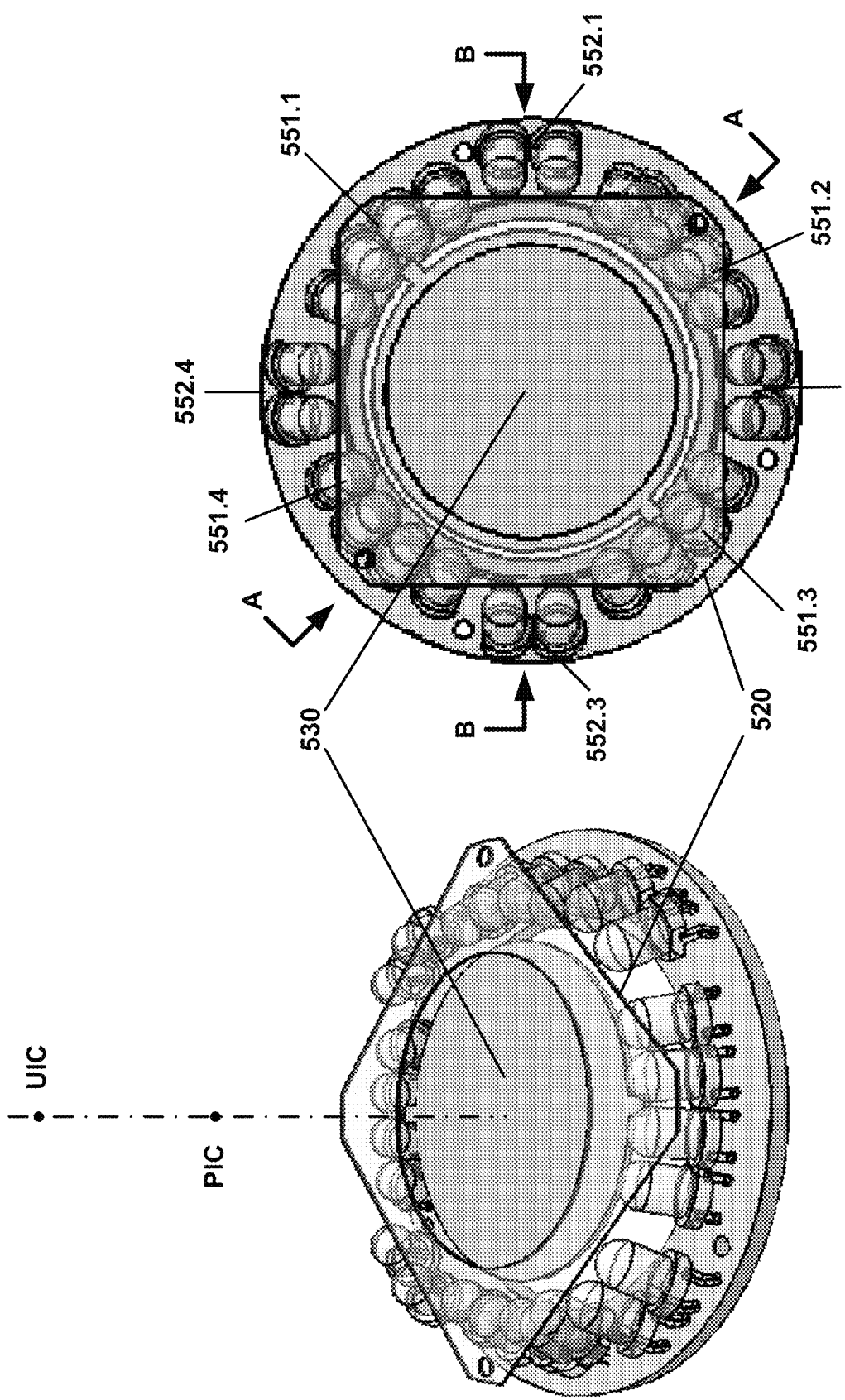

FIGS. 5C and 5D show isometric and plan views respectively of the arrangement of LEDs and polarizers 520 and 530 of sub-assembly 510. FIG. 5C also shows a line through the center of the sub-assembly opening with two points marked thereon. In exemplary embodiments, the LEDs in groups 551 are oriented so that the light emitted therefrom, which passes through polarizer 520, generally converges at the point on the center line labeled PIC (polarized illumination convergence), whereas the LEDs in groups 552 are oriented so that the light emitted therefrom, which does not pass through polarizer 520, generally converges at the point on the center line labeled UIC (unpolarized illumination convergence). Generally, UIC is further from the head 110 than PIC. In operation, with the subject tissue in focus through lens 560, PIC is preferably on or near the surface of the tissue (i.e., PIC is preferably at or near the focal point of lens 560), whereas UIC is preferably beneath the surface of the tissue. This is illustrated in FIGS. 5E and 5F. Such a configuration helps prevent a dark periphery or center when the unpolarized light is projected onto the target tissue. Note that FIG. 5E shows non-contact viewing, whereas FIG. 5F shows contact viewing, with contact viewing element 125 in place. In the case of polarized illumination, it is preferable that the angle of incident polarized light relative to the skin surface (shown in FIG. 5E as angle α) be within a range of approximately 45 to 55 degrees.

It should be noted that in the contact imaging mode, the light emitted from the LEDs passes through the contact viewing element 125, which may act as a partial mirror surface. Preferably, an anti-reflective coating is provided on the inside surface of the front glass in order to minimize the reflection thereon of the LEDs. In addition, at least the LEDs of the groups 552, i.e., the LEDs whose light is not polarized by illumination polarizer 520, are arranged so as to be beyond the inner opening of the contact viewing element 125. As shown in the cross-sectional view of FIG. 5F, the inner extent of the LEDs 552 corresponds to or lies beyond the inner opening of the contact viewing element 125, as represented by lines 126. This relationship can also be seen in FIG. 5B. This prevents the mirror image of these LEDs on the glass of element 125 from being viewed when viewing skin through the head. This is less of a concern for the LEDs of the groups 551, whose emitted light is polarized by illumination polarizer 520, particularly where the illumination polarization is orthogonal to that of viewing polarizer 530. In this case, most of the mirror reflection of the LEDs 551 is attenuated by the orthogonal viewing polarizer. In a contact, unpolarized illumination mode of operation, however, the reflections of LEDs 552 may be too bright and otherwise introduce glare, thereby hindering the viewing of the skin. The placement and/or angling of the LEDs 552, as shown, keeps such mirrored source reflections out of the field of view.

As mentioned above, a variety of illumination configurations are possible. For example, as it may be desirable to provide a more intense polarized illumination than an unpolarized illumination, there may be more groups 551 than groups 552 and/or the number of LEDs in each group 551 may be greater than in each group 552. Moreover, the LEDs in the groups 551 may be selected and/or driven to deliver a more intense illumination than those in the groups 552.

Additionally, as it is desirable to direct the polarized illumination to the center of the field of view, the LEDs in groups 551 can be selected to have a relatively narrow beam angle (e.g., 15-35 degrees). On the other hand, as it is desirable that the unpolarized illumination be distributed uniformly across the field of view, the LEDs in groups 552 can be selected to have a broader beam angle (e.g., 25-65 degrees).

FIGS. 6A and 6B show front and back perspective views, respectively, of a further exemplary device 200 for viewing and imaging tissue such as human skin. The dermatoscope device 200 generally comprises a head portion 210 and a body portion (or "body") 220. The head portion 210 serves to provide viewing, imaging and illumination functionality. The body 220 is configured and sized to be held by hand as a user views the target tissue via the head portion 210. The body 220 also houses circuitry and a power source, such as one or more batteries, for controlling and driving the illumination provided by the head portion 210. In exemplary embodiments, illumination is provided by one or more groups of one or more light emitting diodes (LEDs) each.

The body 220 is configured to receive a mobile computing device 230, such as a smartphone, MP3 player, tablet computer, handheld computer, or the like. The device 230 preferably has a camera and a display. In the illustrated embodiment, the device 230 has a touchscreen display on one side and a camera on the opposite side.

In exemplary embodiments, the head portion 210 has a generally circular head 215 arranged at the end of an arm 217 that pivots relative to the body 220. FIGS. 6A and 6B show the head portion in a first, lowered, position, whereas FIG. 6C shows a rear plan view of the device 200 with the head portion 210 in a second, pivoted position. The device 230 includes a camera with an aperture 235 that is in alignment with the center of the head 215 when the head portion 210 is in the first position, as shown in FIGS. 6A and 6B. When the head portion 210 is in the second position, as shown in FIG. 6C, the head 215 swings clear of the aperture 235 so that the camera can capture images directly, whereas in the first, lowered, position, the camera captures images through the head 215, which may include magnification and have a narrower field of view (FOV) than that of the camera alone.

The illumination function of the head portion 210 can be varied in accordance with its position. For example, when in the first, lowered, position, the illumination function can be in a first mode, whereas in the second position, the illumination function can be in a second mode. The first and second modes may include activated, de-activated, and partially activated modes (e.g., a subset of LEDs activated), as described in greater detail below.

Figure 6I:
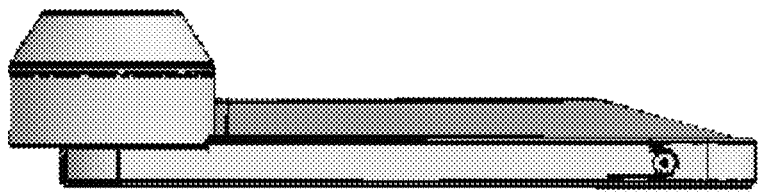
Figure 6H:
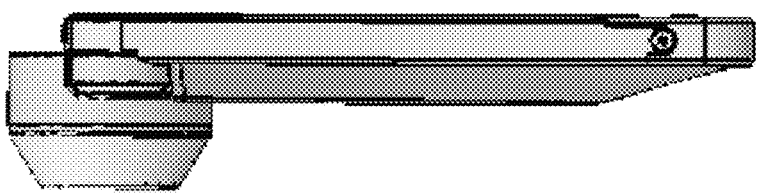
Figure 6E:
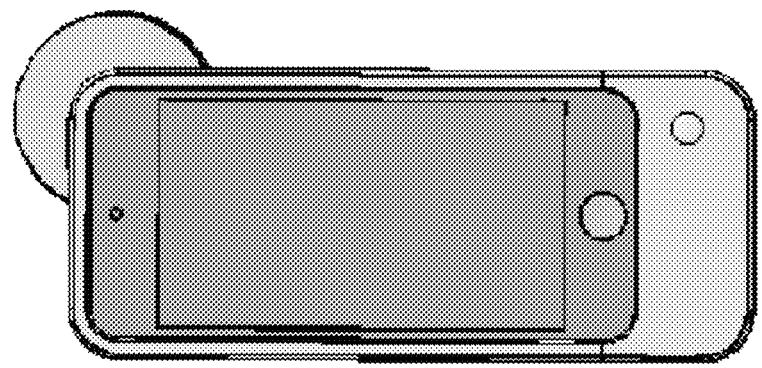
Figure 6G:
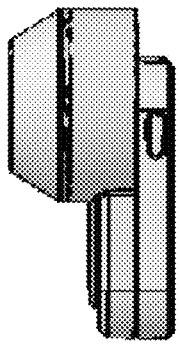
Figure 6D:
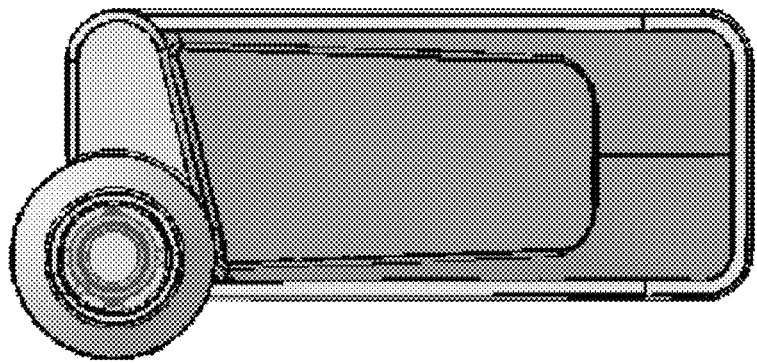
Figure 6F:
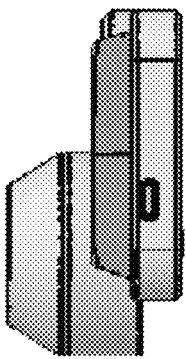

FIGS. 6D and 6E show front and back plan views, respectively, of the device 200. FIGS. 6F and 6G show bottom and top elevation views, respectively, of the device 200, and FIGS. 6H and 6I show right and left side elevation views, respectively, of the device 200.

FIG. 7A shows a rear perspective view of the device 200 with the mobile computing device 230 removed from the body 220. FIG. 7B shows a similar view but with a bottom end piece 225 of the body 220 removed. With the end piece 225 removed, the mobile computing device 230 can be inserted into or removed from the body 220. One or more connectors 227, 228 connect circuitry in the body 220 to the device 230 via one or more ports such as data, power and/or audio ports.

Figure 8C:
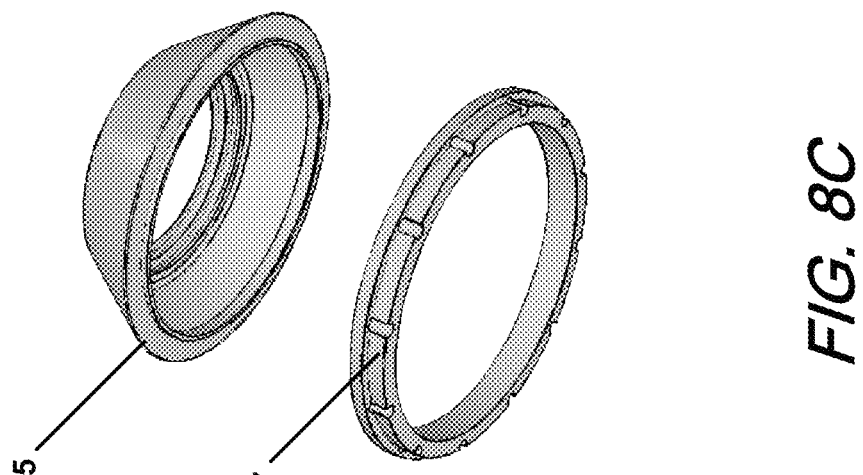
FIGS. 8A through 8C show an exemplary arrangement in which a contact viewing element is removably attached to a head portion of the device of FIGS. 6A-I.
Figure 8B:
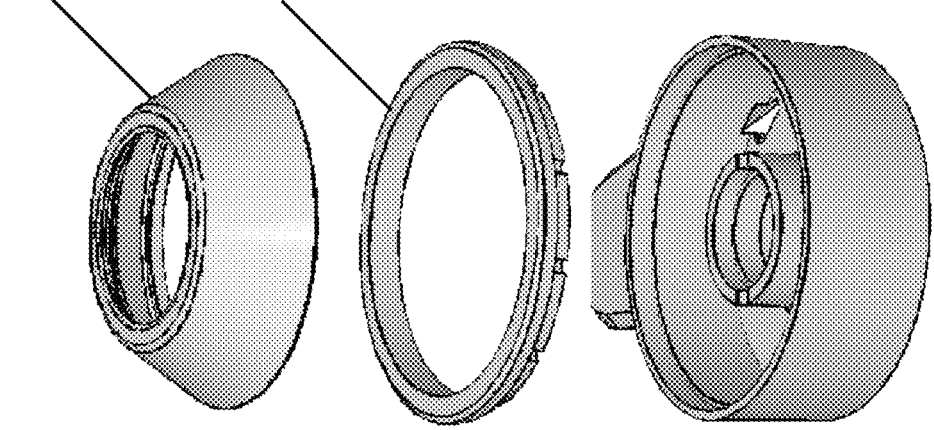
Figure 8A:
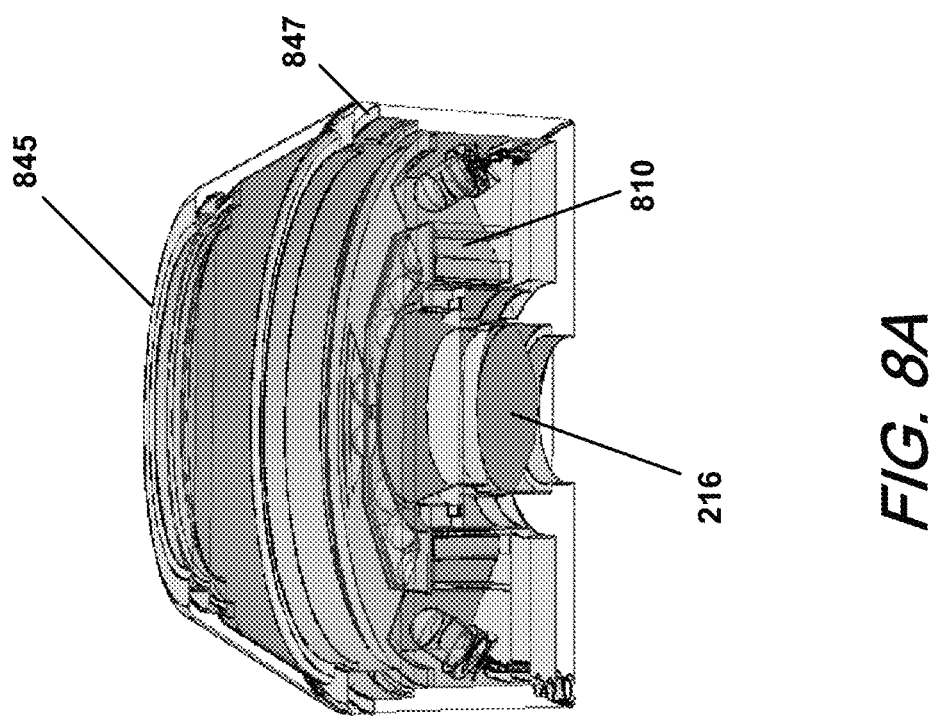

FIG. 8A is an isometric view of a cross-section of head 215 of the device 200. The head 215 has an illumination and polarization sub-assembly 810 similar to that of device 100 with multiple groups of LEDs, an illumination polarizer, and a viewing polarizer. An optical element, such as lens 216 is mounted in the head 215 generally coaxially with the central opening of sub-assembly 810, as shown in FIG. 8A.

Also shown in FIG. 8A is a contact viewing element 845 that can be removably attached to the head 215. More specifically, the contact viewing element 845 magnetically attaches to a ring element 847 of the head 215. FIG. 8A shows the contact viewing element 845 mated with ring element 847. FIGS. 8B and 8C are front and rear perspective views, respectively, of contact viewing element 845 and ring element 847, in isolation. Like element 115 shown in FIGS. 4C and 4D, ring element 847 is provided with a plurality of recesses or pockets for receiving therein a corresponding plurality of magnets. Other attachment arrangements are also possible, as discussed above with respect to element 115.

Note that unlike contact viewing element 125 of FIGS. 4A and B which is substantially planar, element 845 has a generally frustoconically shaped body that places the transparent front plate at a predetermined distance away from head 215 when attached to ring element 847. The predetermined distance is preferably such that the contacted skin surface will be in focus to the camera when viewed via the head 215 of device 200.

Figures 9A, 9B:
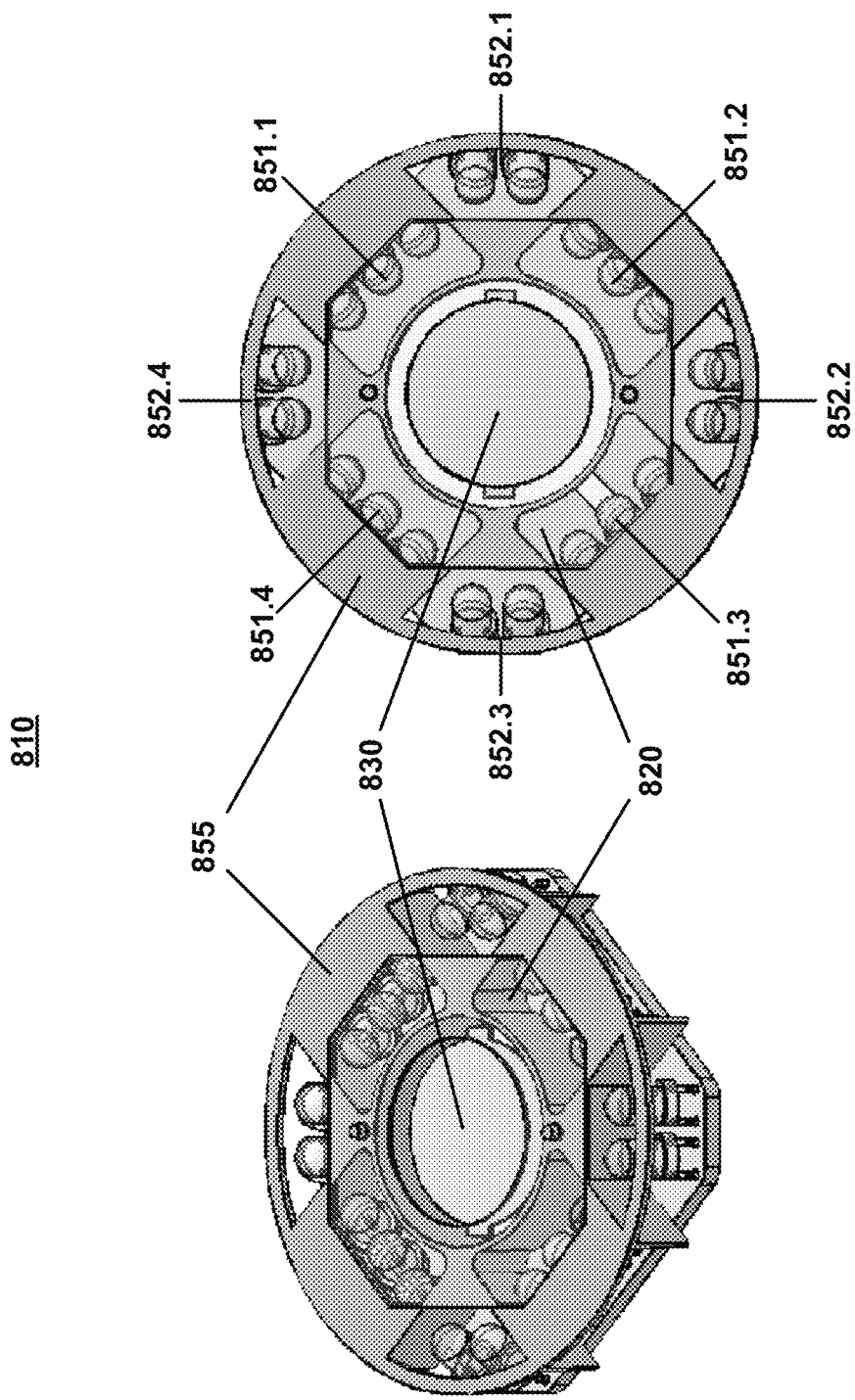
FIGS. 9A and 9B show an exemplary illumination and polarization sub-assembly of the device of FIGS. 6A-I.

FIGS. 9A and 9B show isometric and plan views, respectively, of an illumination and polarization sub-assembly 810 which is located in the head 215 of the device 200. Sub-assembly 810 includes a plurality of illumination sources, such as LEDs arranged about a central opening through which the target tissue is viewed. In the exemplary embodiment shown, there are 20 LEDs arranged in four groups 851 of three LEDs each and in four groups 852 of two LEDs each. As shown, the 12 LEDs in the four groups 851.1-851.4 are arranged generally at a first distance from the center of the center opening, whereas the eight LEDs in the four groups 852.1-852.4 are arranged generally at a second distance from the center of the center opening, with the second distance being greater than the first distance.

Sub-assembly 810 includes an illumination polarizer 820 arranged so that light emitted from the four groups 851 of four LEDs passes through the illumination polarizer 820 whereas light emitted from the four groups 852 of two LEDs does not pass through the illumination polarizer 820. In the exemplary embodiment shown, illumination polarizer 820 has a generally polygonal shape, e.g., square or octagon, with a central opening corresponding to the center opening of the sub-assembly 810.

In exemplary embodiments, the four groups LEDs 851 and the four groups of LEDs 852 can be energized independently of each other.

Sub-assembly 810 includes a shroud component 855 having vertical walls between adjacent groups of LEDs.

Sub-assembly 810 also includes a viewing polarizer 830 arranged generally coaxially with the center opening of the sub-assembly so that light passing through the center opening is polarized.

In exemplary embodiments, illumination polarizer 820 and viewing polarizer 830 are arranged so that their polarization orientations are different. In exemplary embodiments, said orientations are generally orthogonal.

Figure 10:
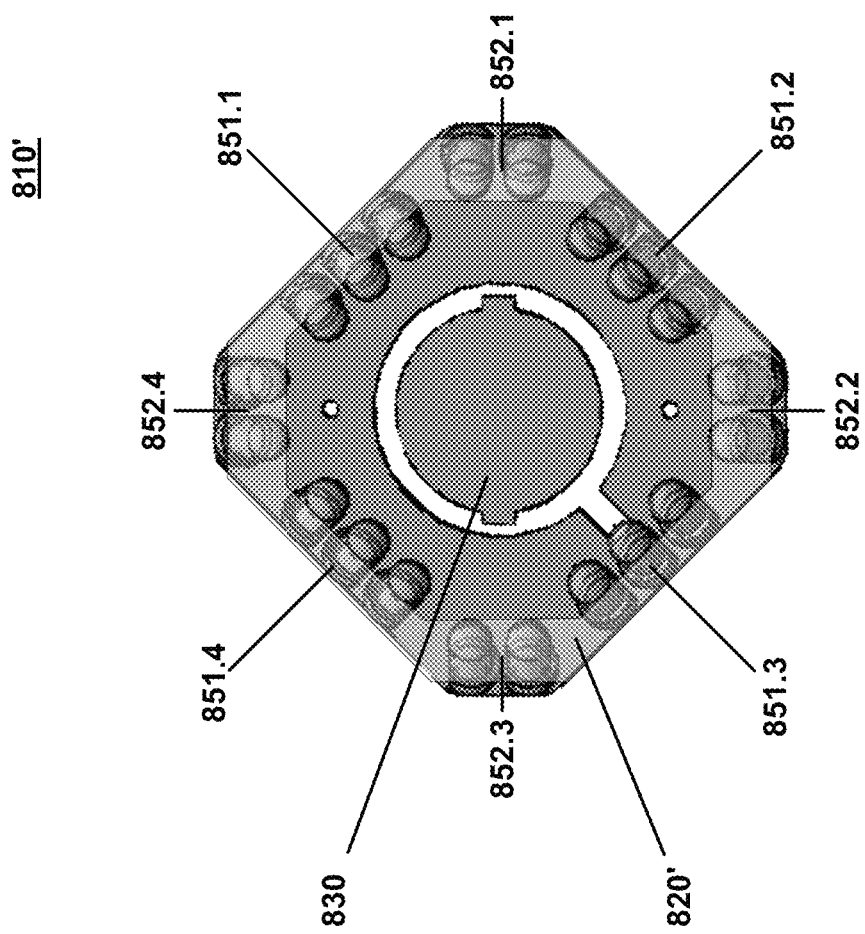
FIG. 10 shows a further exemplary illumination and polarization sub-assembly of the device of FIGS. 6A-I.

FIG. 10 shows a plan view of the illumination and polarization elements, in isolation, of a further exemplary viewing sub-assembly 810' which can be located in the head 215 of the device 200. Note that shroud component 855 has been removed from FIG. 10 for clarity. Like exemplary sub-assembly 810, sub-assembly 810' includes 20 LEDs arranged in four groups 851 of three LEDs each and in four groups 852 of two LEDs each, with the 12 LEDs in the four groups 851.1-851.4 arranged generally at a first distance from the center of the center opening, and the eight LEDs in the four groups 852.1-852.4 arranged generally at a second distance from the center of the center opening, the second distance being greater than the first distance.

Exemplary sub-assembly 810' includes an illumination polarizer 820' configured so that light emitted from the four groups 851 of four LEDs does not pass through the illumination polarizer 820' whereas light emitted from the four groups 852 of two LEDs does pass through the illumination polarizer 820'. In the exemplary embodiment shown, illumination polarizer 820' has a generally polygonal shape, e.g., square or octagon, with a central opening.

In exemplary embodiments, illumination polarizer 820' and viewing polarizer 830 are arranged so that their polarization orientations are different. In exemplary embodiments, said orientations are generally orthogonal.

Figure 11:
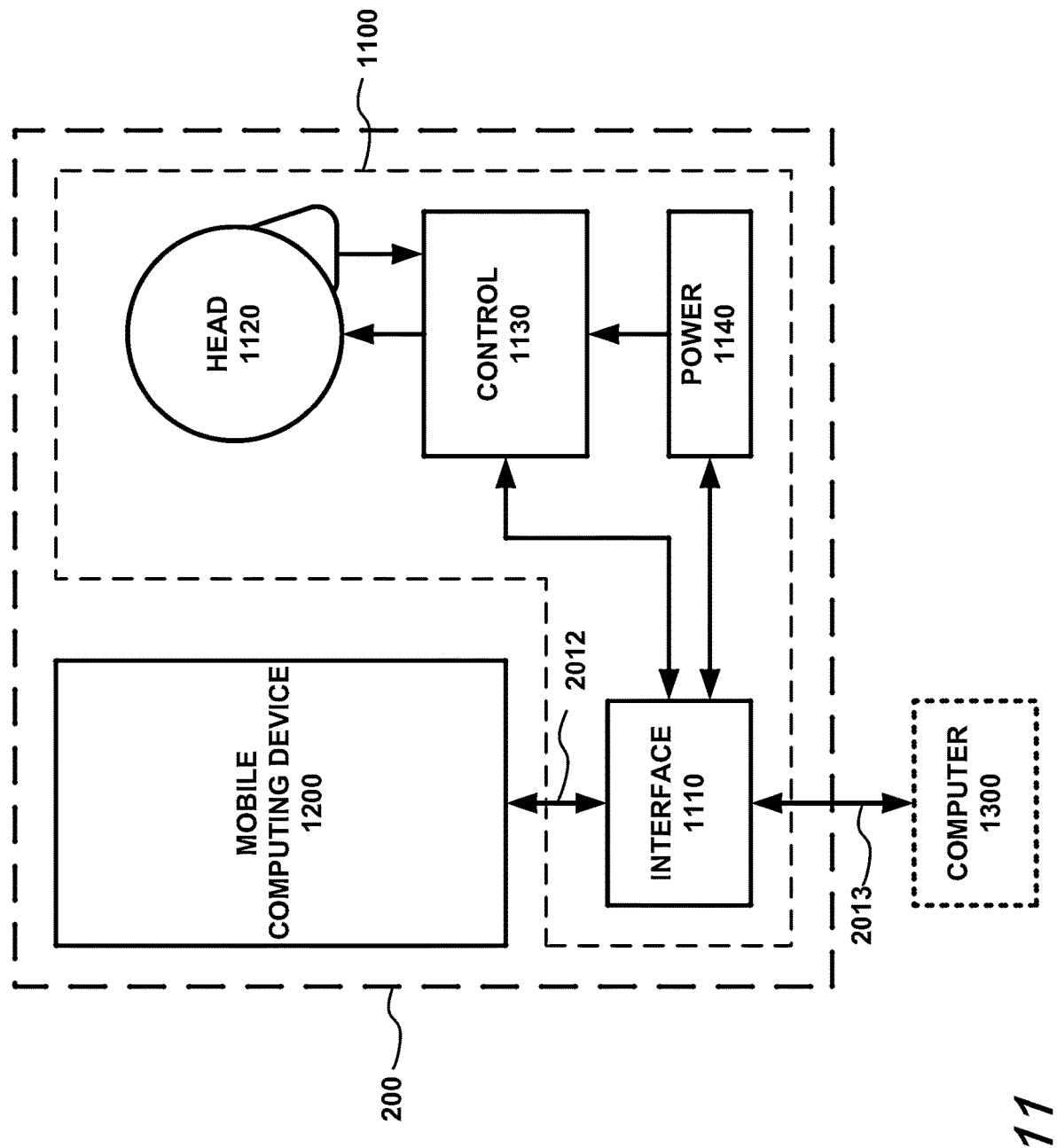
FIG. 11 shows a high-level block diagram of exemplary circuitry for the device of FIGS. 6A-I.

FIG. 11 shows a high-level block diagram of the circuitry of device 200. As shown in FIG. 11, device 200 includes circuitry 1100 which interfaces with a mobile computing device 1200. Circuitry 1100 includes an interface block 1110, head circuitry block 1120, control block 1130 and power block 1140.

In addition to interfacing with mobile computing device 1200 via interface 2012, interface block 1110 may also preferably include an interface 2013 for interfacing with an external computer 1300, or the like. Interface 2013 may include for example, a Universal Serial Bus (USB) interface or the like. Interface block 1110 may also allow mobile computing device 1200 to interconnect with computer 1300. In addition to signals, it is contemplated that power may also be provided via interface 2012 and/or 2013. For example, power may be provided from computer 1300 or other power source via interface 2013 and conveyed by interface block 1110 via interface 2012 to mobile computing device 1200. Interfaces 2012 and/or 2013 may include one or more data, power and/or audio connections and be wired and/or wireless.

Power block 1140, which may comprise one or more batteries or the like, provides power to circuitry 1100 and/or mobile computing device 1200. Power block 1140 may also receive power via interface block 1110, such as for charging rechargeable batteries.

Control block 1130 interacts with interface block 1110 as well as head circuitry block 1120 and may be responsive to user input and/or signals conveyed via interface 2012 and/or 2013. Control block 1130 may include, for example, one or more processors and associated memory. Computer programs, or software, are stored in memory for execution by said processor(s). The memory may include for example, random-access memory (RAM) and/or read-only memory (ROM), may be internal and/or external to circuitry 1100, and may be volatile and/or non-volatile.

It is contemplated that circuitry 1100 may include various input and output devices, such as switches, buttons, sensors, indicators, displays or the like. A sensor or switch, for example, may be provided to sense the position of the head portion 210 and to provide a corresponding indication to control block 1130, which may control the illumination provided by head circuitry 1120 accordingly. Control block 1130 may provide an indication of the position of head portion 210 to mobile computing device 1200 and/or computer 1300 via interface block 1110. Mobile computing device 1200 and/or computer 1300 may be able to control functions of the device, such as the illumination provided by head circuitry 1120, via control block 1130.

The attachment and/or integration of a mobile computing device allow devices such as described above to be used in a variety of applications such as telemedicine, remote diagnosis, and the like. It is contemplated that the mobile computing device 1200 can transmit, receive, store and/or display data and/or images. For example, the mobile computing device can wirelessly and/or through a wired interface transfer the captured images and associated patient or other data to a central database. It can also communicate with other processing elements via the cloud for processing/analyzing the captured images, receive the processed images/analysis results and display them to the user and/or locally store this information.

In view of the above, the foregoing merely illustrates principles of the invention and it will thus be appreciated that those skilled in the art will be able to devise numerous alternative arrangements which, although not explicitly described herein, embody principles of the invention and are within its spirit and scope. It is therefore to be understood that numerous modifications may be made to the illustrative embodiments and that other arrangements may be devised without departing from the spirit and scope of the invention.

What is claimed is:

1. A dermatoscope comprising:
a circular viewing opening;
a plurality of light sources including first and second groups of light sources arranged about the viewing opening;
a first polarizer for polarizing light passing through the viewing opening; and
a second polarizer for polarizing light emitted from the dermatoscope by the first group of light sources, the second polarizer having a central opening aligned with the viewing opening,
wherein the first and second groups of light sources are arranged at different distances from a central axis of the viewing opening so that light emitted by at least one light source of the second group of light sources emerges from the dermatoscope without having been polarized by the second polarizer.

2. The dermatoscope of claim 1, wherein the second group of light sources is arranged at a greater distance from the central axis of the viewing opening than the first group of light sources.

3. The dermatoscope of claim 1, wherein the polarization orientations of the first and second polarizers are mutually orthogonal.

4. The dermatoscope of claim 1, wherein the light sources of the first group are oriented towards a first point along the central axis of the viewing opening and the light sources of the second group are oriented towards a second point along the central axis of the viewing opening, wherein the second point is further away from the dermatoscope than the first point.

5. The dermatoscope of claim 1, wherein the light sources of the second group are beyond an inner opening of a contact viewing element.

6. The dermatoscope of claim 1 comprising a lens in the viewing opening.

7. The dermatoscope of claim 1, wherein the plurality of light sources and the viewing opening are arranged in a pivoting head portion selectively allowing alignment of the viewing opening with the field of view of an image capture device.

8. The dermatoscope of claim 7, wherein an operating mode of at least a subset of the plurality of light sources is controlled in accordance with a position of the pivoting head.

9. The dermatoscope of claim 1 comprising a selectively extendable element that can be selectively extended coaxially with the viewing opening.

10. The dermatoscope of claim 1 comprising a removable contact element for contacting a surface to be viewed.

11. The dermatoscope of claim 10, wherein the removable contact element includes a frustoconical extension.

12. The dermatoscope of claim 1, wherein the first group of light sources includes a plurality of first sub-groups of light sources and the second group of light sources includes a plurality of second sub-groups of light sources, the first and second sub-groups of light sources being alternately arranged adjacent to each other about the viewing opening.

13. The dermatoscope of claim 12 comprising a shroud element for blocking light leakage between adjacent first and second groups of light sources.

14. The dermatoscope of claim 1, wherein at least one of the second polarizer or the central opening of the second polarizer has a polygonal shape.

15. The dermatoscope of claim 1, wherein the first and second groups of light sources are arranged at different distances from a central axis of the viewing opening so that light emitted by at least one light source of the second group of light sources clears an outer edge of the second polarizer or passes through the central opening of the second polarizer.

16. A dermatoscope comprising:
a head portion including:
a circular viewing opening, and
a plurality of light sources arranged about the viewing opening; and
a body portion including an image capture device;
circuitry that controls an operating mode of at least one of the plurality of light sources in accordance with a position of the head portion relative to the body portion,
wherein the head portion is pivotally attached to the body portion selectively allowing alignment of the viewing opening with the field of view of the image capture device.

17. The dermatoscope of claim 16, wherein the head portion includes a removable contact element for contacting a surface to be viewed.

18. The dermatoscope of claim 17, wherein the removable contact element includes a frustoconical extension.

* * * * *